United States Patent
Tomatsu et al.

(10) Patent No.: US 8,034,919 B2
(45) Date of Patent: Oct. 11, 2011

(54) PROBE, PROBE SET, PROBE CARRIER, AND TESTING METHOD

(75) Inventors: Nobuhiro Tomatsu, Yokohama (JP); Toshifumi Fukui, Yokohama (JP); Nobuyoshi Shimizu, Sakura (JP); Atsushi Takayanagi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 517 days.

(21) Appl. No.: 12/120,141

(22) Filed: May 13, 2008

(65) Prior Publication Data

US 2008/0293063 A1 Nov. 27, 2008

(30) Foreign Application Priority Data

May 14, 2007 (JP) .................... 2007-128484

(51) Int. Cl.
C07H 21/04 (2006.01)
C07K 16/00 (2006.01)
C12P 21/08 (2006.01)
A61K 39/00 (2006.01)
A61K 39/38 (2006.01)

(52) U.S. Cl. ............... 536/24.32; 424/184.1; 424/274.1; 435/341; 530/388.5; 536/24.3; 536/24.31; 536/24.33

(58) Field of Classification Search .................. None
See application file for complete search history.

(56) References Cited

U.S. PATENT DOCUMENTS

| | | | |
|---|---|---|---|
| 5,512,446 A | 4/1996 | Miyazaki et al. | |
| 5,700,647 A | 12/1997 | Miyazaki et al. | |
| 5,846,730 A | 12/1998 | Miyazaki et al. | |
| 2004/0241643 A1 | 12/2004 | Yamamoto et al. | |
| 2007/0134702 A1 | 6/2007 | Fukui et al. | |
| 2008/0113363 A1 | 5/2008 | Fukui et al. | |
| 2008/0113364 A1 | 5/2008 | Fukui et al. | |
| 2008/0113365 A1 | 5/2008 | Kuribayashi et al. | |
| 2008/0113366 A1 | 5/2008 | Kuribayashi et al. | |
| 2008/0124733 A1 | 5/2008 | Fukui et al. | |
| 2008/0161192 A1 | 7/2008 | Yoshii et al. | |
| 2008/0286791 A1 | 11/2008 | Tomatsu et al. | |
| 2008/0286792 A1 | 11/2008 | Tomatsu et al. | |
| 2008/0287312 A1 | 11/2008 | Tomatsu et al. | |
| 2008/0293061 A1 | 11/2008 | Tomatsu et al. | |

(Continued)

FOREIGN PATENT DOCUMENTS

JP 8-89254 4/1996

(Continued)

OTHER PUBLICATIONS

Makimura et al., (J. of Clinical Microbio. 1998. vol. 36(9):2629-2633).*

(Continued)

*Primary Examiner* — Albert Navarro
*Assistant Examiner* — Ja'Na Hines
(74) *Attorney, Agent, or Firm* — Fitzpatrick, Cella, Harper & Scinto

(57) ABSTRACT

A probe, a set of probes, and a probe carrier on which the probe or the set of probes is immobilized, are provided for classification of fungus species. The probe or the set of probes is capable of collectively detecting fungus of the same species and distinguishingly detecting those fungus from fungus of other species. The probe is an oligonucleotide probe for detecting a pathogenic fungus DNA and includes at least one of base sequences of SEQ ID NOS. 1 to 4 and mutated sequences thereof.

7 Claims, 2 Drawing Sheets

U.S. PATENT DOCUMENTS

| | | |
|---|---|---|
| 2008/0293062 A1 | 11/2008 | Tomatsu et al. |
| 2008/0293064 A1 | 11/2008 | Tomatsu et al. |
| 2008/0293065 A1 | 11/2008 | Tomatsu et al. |
| 2008/0293066 A1 | 11/2008 | Tomatsu et al. |
| 2008/0293067 A1 | 11/2008 | Tomatsu et al. |
| 2008/0299569 A1 | 12/2008 | Tomatsu et al. |
| 2008/0299570 A1 | 12/2008 | Tomatsu et al. |
| 2008/0299571 A1 | 12/2008 | Tomatsu et al. |
| 2008/0299572 A1 | 12/2008 | Tomatsu et al. |
| 2008/0299573 A1 | 12/2008 | Tomatsu et al. |
| 2008/0299574 A1 | 12/2008 | Tomatsu et al. |
| 2008/0299575 A1 | 12/2008 | Tomatsu et al. |
| 2008/0299576 A1 | 12/2008 | Tomatsu et al. |
| 2008/0299577 A1 | 12/2008 | Tomatsu et al. |
| 2008/0299578 A1 | 12/2008 | Tomatsu et al. |
| 2008/0305487 A1 | 12/2008 | Tomatsu et al. |
| 2008/0305488 A1 | 12/2008 | Tomatsu et al. |
| 2009/0004659 A1 | 1/2009 | Tomatsu et al. |
| 2009/0011419 A1 | 1/2009 | Tomatsu et al. |
| 2009/0068661 A1 | 3/2009 | Tomatsu et al. |
| 2009/0081666 A1 | 3/2009 | Fukui et al. |

FOREIGN PATENT DOCUMENTS

| | | |
|---|---|---|
| JP | 2004-313181 | 11/2004 |

OTHER PUBLICATIONS

Martin et al., (J. of Clin. Microbio. 2000. vol. 38(10): 3735-3742).*
Accession No. DQ860810 submitted Jul. 20, 2006.*
Makimura et al., (J. of Clinical Microbio. 1999. vol. 37(4):920-924).*
Iwen et al., Medical Mycology. 2002. vol. 40:87-109 in view of Makimura et al., (J. of Clinical Microbio. 1999. vol. 37(4):920-924).*

U.S. Appl. No. 12/295,276, filed Mar. 30, 2007, Applicants: Hideto Kuribayashi, et al.
U.S. Appl. No. 12/294,915, filed Mar. 30, 2007, Applicants: Hideto Kuribayashi, et al.
U.S. Appl. No. 12/295,277, filed Mar. 30, 2007, Applicants: Toshifumi Fukui, et al.
U.S. Appl. No. 12/295,273, filed Mar. 30, 2007, Applicants: Hideto Kuribayashi, et al.
U.S. Appl. No. 12/294,910, filed Mar. 30, 2007, Applicants: Hideto Kuribayashi, et al.
U.S. Appl. No. 12/294,914, filed Mar. 30, 2007, Applicant(s): Toshifumi Fukui, et al.
U.S. Appl. No. 12/295,581, filed Mar. 30, 2007, Applicant(s): Hideto Kuribayashi, et al.
U.S. Appl. No. 12/295,584, filed Mar. 30, 2007, Applicant(s): Toshifumi Fukui, et al.
U.S. Appl. No. 12/295,583, filed Mar. 30, 2007, Applicant(s): Toshifumi Fukui, et al.
U.S. Appl. No. 12/295,579, filed Mar. 30, 2007, Applicant(s): Toshifumi Fukui, et al.
U.S. Appl. No. 11/935,930, filed Nov. 6, 2007, Applicant(s): Hiroto Yoshii, et al.
U.S. Appl. No. 11/935,807, filed Nov. 6, 2007, Applicant(s): Hideto Kuribayashi, et al.
U.S. Appl. No. 11/935,789, filed Nov. 6, 2007, Applicant(s): Toshifumi Fukui, et al.
U.S. Appl. No. 11/935,820, filed Nov. 6, 2007, Applicant(s): Hideto Kuribayashi, et al.
U.S. Appl. No. 11/935,849, filed Nov. 6, 2007, Applicant(s): Hiroto Yoshii, et al.
U.S. Appl. No. 12/120,172, filed May 13, 2008, Applicant(s): Nobuhiro Tomatsu, et al.

* cited by examiner

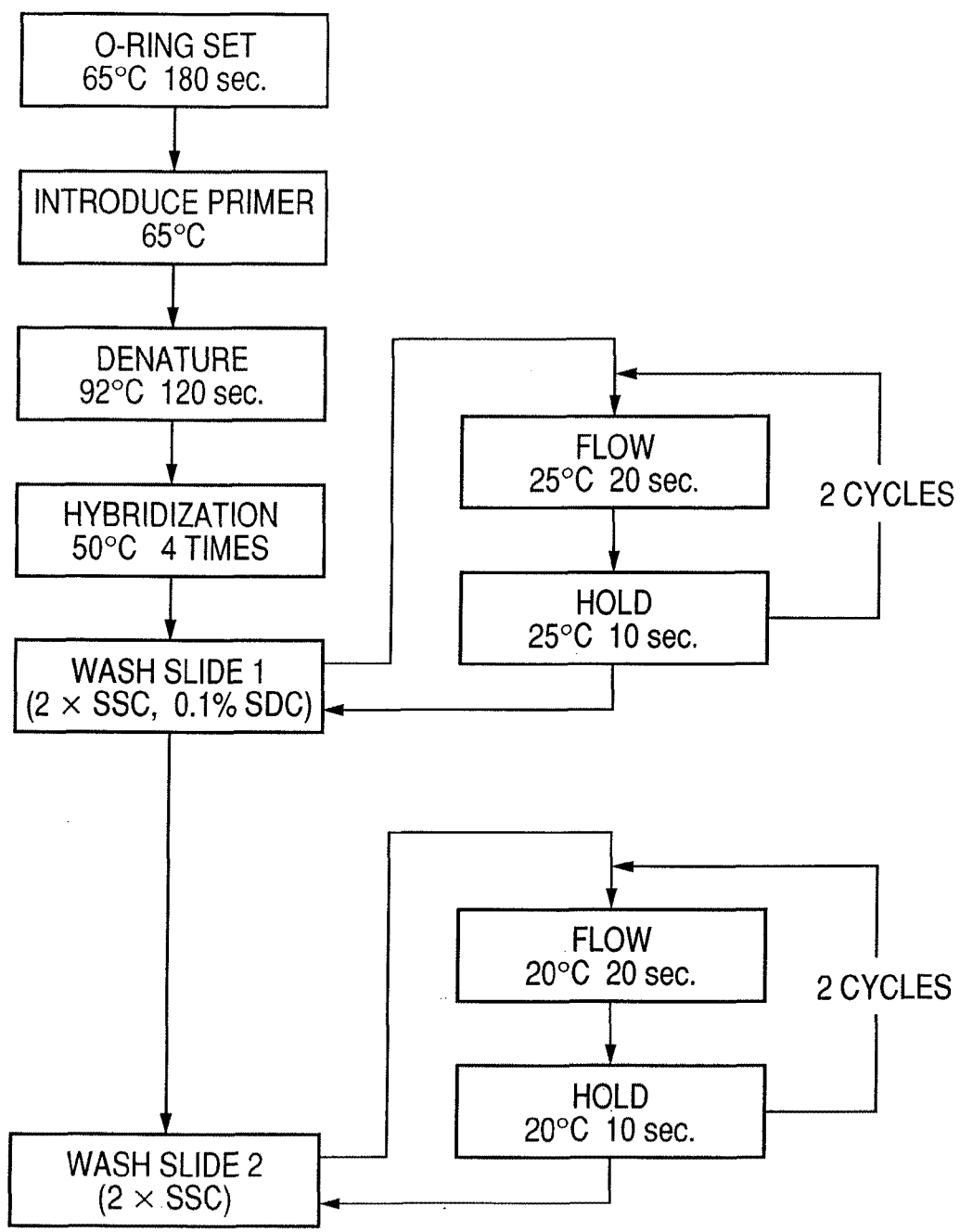

SEQUENCE LISTING

```
<160> NUMBER OF SEQ ID NOS: 7

<210> SEQ ID NO 1
<211> LENGTH: 22
<212> TYPE: DNA
<213> ORGANISM: Artificial Sequence
<220> FEATURE:
<223> OTHER INFORMATION: Probe

<400> SEQUENCE: 1
agcctctttg ggggctttag ct                                              22

<210> SEQ ID NO 2
<211> LENGTH: 29
<212> TYPE: DNA
<213> ORGANISM: Artificial Sequence
<220> FEATURE:
<223> OTHER INFORMATION: Probe

<400> SEQUENCE: 2
acagacatca aaaaatcttg gaaagctgt                                       29

<210> SEQ ID NO 3
<211> LENGTH: 22
<212> TYPE: DNA
<213> ORGANISM: Artificial Sequence
<220> FEATURE:
<223> OTHER INFORMATION: Probe

<400> SEQUENCE: 3
ctgggcgaat gggcagtcaa ac                                              22

<210> SEQ ID NO 4
<211> LENGTH: 22
<212> TYPE: DNA
<213> ORGANISM: Artificial Sequence
```

```
<220> FEATURE:
<223> OTHER INFORMATION: Probe

<400> SEQUENCE: 4
ctctggcctt cccccaaatc tc                                        22

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
tccgtaggtg aacctgcgg                                            19

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tcctccgctt attgatatgc                                           20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
tcctccgctt attgatatgc                                           20
```

PROBE, PROBE SET, PROBE CARRIER, AND TESTING METHOD

BACKGROUND OF THE INVENTION

1. Field of the Invention

The present invention relates to a probe and a probe set for detecting a DNA of a pathogenic fungus, *Arthroderma benhamiae*, which are useful for detection and identification of a causative fungus of an infectious disease, and to a probe carrier on which the probe or the probe set is immobilized. The present invention also relates to a DNA testing method and a DNA testing kit using the same.

2. Description of the Related Art

Heretofore, reagents for and methods of quickly and accurately detecting pathogenic fungi in a sample have been proposed. For instance, Japanese Patent Application Laid-Open No. H08-089254 discloses oligonucleotides having specific base sequences, which can be used as probes and primers for detecting pathogenic fungi of candidiasis and aspergillosis, and a method of detecting target fungi using such oligonucleotides. In addition, the same patent document also discloses a primer set used for PCR amplifying a plurality of target fungi in common. Further, the same patent document also discloses a method of identifying fungus species in a sample comprising subjecting a plurality of target fungi in the sample to PCR amplification using the primer set, and then detecting the sequence portions specific to the respective fungi by a hybridization assay using the probes specific to the respective fungi.

On the other hand, a method capable of simultaneously detecting a plurality of oligonucleotides having different base sequences is known. The method uses a probe array in which probes having sequences complementary to the respective base sequences are arranged at intervals on a solid phase (Japanese Patent Application Laid-Open No. 2004-313181).

SUMMARY OF THE INVENTION

However, it is not easy to establish a probe which specifically detects a DNA of a pathogenic fungus in a sample. The sample may contain not only the DNA of the pathogenic fungus but also DNAs of other pathogenic fungi. Thus, it is not easy to establish a probe that specifically detects a DNA of a pathogenic fungus which is less susceptible to the influence of the presence of DNAs of other pathogenic fungi (i.e. cross contamination). Under such circumstances, the inventors of the present invention have conducted investigation on probes for detecting the following pathogenic fungi. The object of the investigation was to obtain probes capable of detecting a DNA of a target pathogenic fungus with a high degree of accuracy even for an analyte containing DNAs of a plurality of fungi with a less cross-contamination level. As a result, a plurality of probes capable of detecting a pathogenic fungus DNA with a high degree of accuracy were finally obtained.

*Arthroderma benhamiae*

A first object of the present invention is to provide a probe and a probe set which are capable of accurately identifying the DNA of a target fungus.

Another object of the present invention is to provide a probe carrier which is capable of accurately identifying a target fungus from a sample in which various kinds of fungi may exist together.

Still another object of the present invention is to provide a DNA testing method for a pathogenic fungus, which can more quickly and more accurately detect a target fungus from a sample when various kinds of fungi exist in the sample, and to provide a kit for the testing method.

The probe of the present invention for detecting a DNA of *Arthroderma benhamiae* which is a pathogenic fungus includes one of the following base sequences (1) to (5):

(1) agcctctttgggggctttagct (SEQ ID NO. 1) or a complementary sequence thereof;

(2) acagacatcaaaaaatcttggaaagctgt (SEQ ID NO. 2) or a complementary sequence thereof;

(3) ctgggcgaatgggcagtcaaac (SEQ ID NO. 3) or a complementary sequence thereof;

(4) ctctggccttcccccaaatctc (SEQ ID NO. 4) or a complementary sequence thereof; and (5) a mutated sequence which is obtained by deletion, substitution, or addition of a base on one of the sequences of SEQ ID NOS. 1 to 4 and the complementary sequences thereof in a range that the mutated sequence retains a function as the probe.

In addition, the probe set of the present invention for detecting a DNA of *Arthroderma benhamiae* which is a pathogenic fungus includes at least two of the following probes (A) to (P):

(A) a probe including a base sequence represented by agcctctttgggggctttagct (SEQ ID NO. 1);

(B) a probe including a base sequence represented by acagacatcaaaaaatcttggaaagctgt (SEQ ID NO. 2);

(C) a probe including a base sequence represented by ctgggcgaatgggcagtcaaac (SEQ ID NO. 3);

(D) a probe including a base sequence represented by ctctggccttcccccaaatctc (SEQ ID NO. 4);

(E) a probe including a complementary sequence of SEQ ID NO. 1;

(F) a probe including a complementary sequence of SEQ ID NO. 2;

(G) a probe including a complementary sequence of SEQ ID NO. 3;

(H) a probe including a complementary sequence of SEQ ID NO. 4;

(I) a probe including a mutated sequence obtained by deletion, substitution or addition of a base on SEQ ID NO. 1 within a range that the mutated sequence retains a function as the probe;

(J) a probe including a mutated sequence obtained by deletion, substitution or addition of a base on SEQ ID NO. 2 within a range that the mutated sequence retains the function as the probe;

(K) a probe including a mutated sequence obtained by deletion, substitution or addition of a base on SEQ ID NO. 3 within a range that the mutated sequence retains the function as the probe;

(L) a probe including a mutated sequence obtained by deletion, substitution or addition of a base on SEQ ID NO. 4 within a range that the mutated sequence retains the function as the probe;

(M) a probe including a mutated sequence obtained by deletion, substitution or addition of a base on the complementary sequence of SEQ ID NO. 1 within a range that the mutated sequence retains the function as the probe;

(N) a probe including a mutated sequence obtained by deletion, substitution or addition of a base on the complementary sequence of SEQ ID NO. 2 within a range that the mutated sequence retains the function as the probe;

(O) a probe including a mutated sequence obtained by deletion, substitution or addition of a base on the complementary sequence of SEQ ID NO. 3 within a range that the mutated sequence retains the function as the probe; and (P) a probe including a mutated sequence obtained by deletion, substitution or addition of a base on the complementary sequence of SEQ ID NO. 4 within a range that the mutated sequence retains the function as the probe.

The probe carrier of the present invention includes a carrier on which the probe or each of the plurality of probes constituting the probe set mentioned above is placed on a carrier.

In the probe carrier of the present invention, at least one of the probes (A) to (P) is immobilized on a carrier, and when a plurality of probes is to be immobilized, the respective probes are placed while being isolated from each other.

The method of detecting DNA of *Arthroderma benhamiae* in a sample by using a probe carrier according to the present invention includes:

(i) reacting the sample with the probe carrier; and
(ii) detecting a reaction intensity of a probe on the probe carrier reacted with a nucleic acid contained in the sample.

The kit for detecting a pathogenic fungus of the present invention is a kit for detecting a DNA of *Arthroderma benhamiae*, including at least one of the probes (A) to (P) or a probe carrier on which at least one of those probes is immobilized and a reagent for detecting a reaction of a probe with a target nucleic acid.

According to the present invention, when a specimen is infected with the causative fungus mentioned above, the fungus can be more quickly and precisely identified from the specimen even if the specimen is simultaneously and complexly infected with other fungi in addition to the above-mentioned fungus. In particular, *Arthroderma benhamiae* can be detected while precisely distinguishing it from any of fungi of other *Candida* species, fungi of *Trichosporon* species, fungi of *Cryptococcus* species, fungi of *Aspergillus* species, fungi of *Epidermophyton* species, fungi of *Arthroderma* species, and fungi of *Trichophyton* species, which may be more likely to cause cross contamination.

Further features of the present invention will become apparent from the following description of exemplary embodiments with reference to the attached drawings.

BRIEF DESCRIPTION OF THE DRAWINGS

FIG. 3 is a diagram illustrating a protocol of hybridization.

DESCRIPTION OF THE EMBODIMENTS

Figure 1:
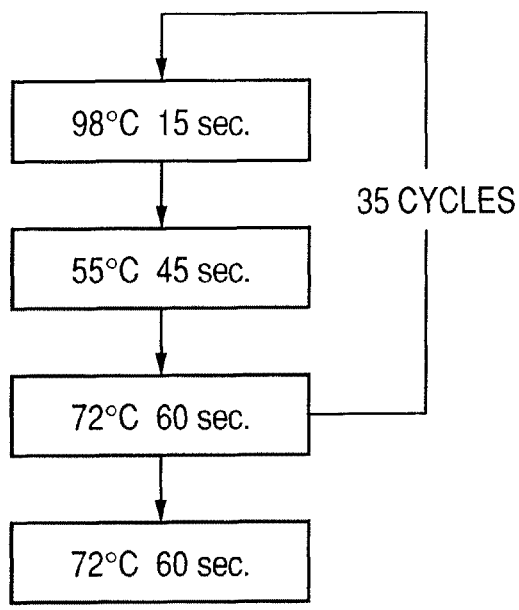
FIG. 1 is a diagram illustrating a 1st PCR protocol.

The present invention provides an oligonucleotide probe for identifying a pathogenic fungus (hereinafter, simply referred to as a probe) and a probe set including a combination of two or more probes. The use of such a probe or a probe set allows the detection of the following fungus which will cause inflammation by infection.

(Fungus Name)
*Arthroderma benhamiae*

The probe of the present invention can react with the DNA sequence of an internal transcribed spacer (ITS) of the pathogenic fungus or a nucleic acid having a base sequence specific to the ITS region contained in a sample. The probe can be selected from the oligonucleotides having the following base sequences:

(A) a probe including a base sequence represented by agcctctttgggggctttagct (SEQ ID NO. 1);
(B) a probe including a base sequence represented by acagacatcaaaaaatcttggaaagctgt (SEQ ID NO. 2);
(C) a probe including a base sequence represented by ctgggcgaatgggcagtcaaac (SEQ ID NO. 3);
(D) a probe including a base sequence represented by ctctggccttcccccaaatctc t (SEQ ID NO. 4);

(E) a probe including a complementary sequence of the base sequence represented by SEQ ID NO. 1;
(F) a probe including a complementary sequence of the base sequence represented by SEQ ID NO. 2;
(G) a probe including a complementary sequence of the base sequence represented by SEQ ID NO. 3;
(H) a probe including a complementary sequence of the base sequence represented by SEQ ID NO. 4;
(I) a probe including a mutated sequence obtained by deletion, substitution or addition of a base on SEQ ID NO. 1 in a range that the mutated sequence retains a function as the probe;
(J) a probe including a mutated sequence obtained by deletion, substitution or addition of a base on SEQ ID NO. 2 in a range that the mutated sequence retains the function as the probe;
(K) a probe including a mutated sequence obtained by deletion, substitution or addition of a base on SEQ ID NO. 3 in a range that the mutated sequence retains the function as the probe;
(L) a probe including a mutated sequence obtained by deletion, substitution or addition of a base on SEQ ID NO. 4 in a range that the mutated sequence retains the function as the probe;
(M) a probe including a mutated sequence obtained by deletion, substitution or addition of a base on SEQ ID NO. 1 in a range that the mutated sequence retains the function as the probe;
(N) a probe including a mutated sequence obtained by deletion, substitution or addition of a base on the complementary sequence of SEQ ID NO. 2 in a range that the mutated sequence retains the function as the probe;
(O) a probe including a mutated sequence obtained by deletion, substitution or addition of a base on the complementary sequence of SEQ ID NO. 3 in a range that the mutated sequence retains the function as the probe; and
(P) a probe including a mutated sequence obtained by deletion, substitution or addition of a base on the complementary sequence of SEQ ID NO. 4 in a range that the mutated sequence retains the function as the probe.

The probe set can be prepared using two or more of those probes. The ITS region of DNA of the pathogenic fungus can be sufficiently detected using the probe set of the present invention.

The mutated sequences include any mutation as far as it does not impair the function of the probe, or any mutation as far as it hybridizes with a nucleic acid sequence of interest as a detection target. Of those, it is desirable to include any mutation as far as it can hybridize with a nucleic acid sequence of interest as a detection target under stringent conditions. Preferable hybridization conditions confining the mutation include those represented in examples as described below. Here, the term "detection target" used herein may be one included in a sample to be used in hybridization, which may be a unique base sequence to the pathogenic fungus, or may be a complementary sequence to the unique base sequence. Further, the variation may be a mutated sequence obtained by deletion, substitution, or addition of at least one base as far as it retains function as the probe.

The characteristics of those probes depend on the specificities of the respective probe sequences to the target nucleic acid sequence as a test object. The specificity of the probe sequence can be evaluated from the degree of coincidence between the base sequence thereof and the target nucleic acid sequence and the melting temperature of a duplex of the target nucleic acid sequence and the probe sequence. In addition, when the probe is constituting a probe set, the performance of the probe also depends on a difference between the melting temperature of the probe and the melting temperature of another probe sequence in the probe set.

For designing these probe sequences, base sequences with high specificities to the same fungus species but with less variation between different strains in the same species may be selected. In addition, a region can be selected to have three or more unmatched bases with respect to the sequence of the fungus species other than the fungus species of interest. Further, it is designed such that the difference between the melting temperature of the duplex of the probe sequence and the sequence of the fungus species of interest and the melting temperature of the duplex of the probe sequence and the sequence of any fungus species other than the species of interest is 10° C. or more. Further, it is designed such that any base is deleted from or added to the highly specific region to hold the melting temperatures of the respective probes immobilized on the same carrier within a predetermined temperature range.

The experiment conducted by the inventors of the present invention has revealed that the attenuation of hybridization intensity may be small when 80% or more of the continuous base sequence is conserved. Therefore, of the probe sequence disclosed in the present application, any mutated sequence may retain the functions of the probe as long as the mutated sequence conserves 80% or more of the continuous base sequence.

Those probe sequences are specific to the DNA sequence of the ITS region of the fungus of interest, so a sufficient hybridization sensitivity to the sequence is expected. In addition, those probe sequences are designed so that it will bring a good result by forming a stable hybrid in a hybridization reaction with a target specimen even in a state of being immobilized on a carrier. Further, those probes are designed so that the melting temperature thereof falls within a predetermined temperature range.

Further, those probe sequences are designed so that fungus species can be determined with a combination of specific portions without determining the sequence of the entire ITS region.

Further, a probe carrier (e.g., DNA chip), on which the probe for detecting a pathogenic fungus of the present invention is immobilized, can be obtained by supplying the probe on a predetermined position on the carrier and immobilizing the probe thereon. Various methods can be used for the supply of probe to the carrier. For example, a method which can be suitably used is to keep the probe in a state of being immobilized on the carrier through a chemical bonding (e.g., covalent bonding) and a liquid containing the probe is then provided on a predetermined position by an inkjet method. Such a method allows the probe to be hardly detached from the carrier and exerts an additional effect of improving the sensitivity. In other words, when a stamping method conventionally called a Stanford method in common use is employed to make a DNA chip, the resultant DNA chip has a disadvantage in that the applied DNA tends to be peeled off. In addition, one of the methods of producing DNA chips is to carry out the placement of probes by the synthesis of DNA on the surface of a carrier (e.g., Oligonucleotide array manufactured by Affymetrix Co., Ltd.). In the method of synthesizing the probe on the carrier, it is difficult to control synthesis amount for each probe. Thus, the amount of immobilized probe per immobilization area (spot) for each probe tends to vary considerably from one another. Such variations in amounts of the respective immobilized probes may cause inaccurate evaluation on the results of the detection with those probes. Based on this fact, the probe carrier of the present invention is preferably prepared using the inkjet method. The inkjet method as described above has an advantage in that the probe can be stably immobilized on the carrier and hardly detaching from the carrier to efficiently provide a probe carrier which can be detected with high sensitivity and high accuracy.

For using a plurality of probes immobilized on a carrier, the probes are designed to have a given melting temperature to simplify the protocol of hybridization.

Hereinafter, preferred embodiments of the present invention will be described in further detail with reference to the attached drawings.

First, the terms used herein will be elucidated as follows:

The term "specimen" represents one obtained as a target of an examination. The term "analyte" represents one prepared from the analyte to contain DNA or nucleic acid fragments. The term "sample" represents a target to be reacted with a probe. The "sample" includes the specimen when the specimen is directly reacted with a probe. The "sample" includes the analyte when the analyte prepared from the specimen is directly reacted with a probe.

The specimen to be tested using probe carriers (e.g., DNA chips) in which the probes of the present invention are immobilized on carriers include those originated from humans and animals such as domestic animals. For example, the test object is any of those which may contain fungi including: any body fluids such as blood, cerebrospinal fluid, expectorated sputum, gastric juice, vaginal discharge, and oral mucosal fluid; tissues such as skin, fingernails, and hair; and excretions such as urine and feces. All media, which can be contaminated with fungi, can be also subjected to a test using the DNA chip. The media include: food, drink water, and water in the natural environment such as hot spring water, which may cause food poisoning by contamination; filters of air cleaners and the like; and the like. Animals and plants, which should be quarantined in import/export, are also used as specimens of interest.

When the specimen as described above can be directly used in reaction with the DNA chip, it is used as a sample to react with the DNA chip and the result of the reaction is then analyzed. Further, when the specimen cannot be directly reacted with the DNA chip, the analyte was subjected to extraction, purification, and other procedures for obtaining a target substance as required and then provided as a sample to carry out a reaction with the DNA chip. For instance, when the specimen contains a target nucleic acid, an extract, which may be assumed to contain such a target nucleic acid, is prepared from a specimen, and then washed, diluted, or the like to obtain an analyte as a sample followed by reaction with the DNA chip. Further, when a target nucleic acid is included in a specimen obtained by carrying out various amplification procedures such as PCR amplification, the target nucleic acid may be a sample for being amplified and then reacted with a DNA chip. Such analytes of amplified nucleic acids include the following.

(a) An amplified analyte prepared by using a PCR-reaction primer designed for detecting ITS region.

(b) An amplified analyte prepared by an additional PCR reaction or the like from a PCR-amplified product.

(c) An analyte prepared by an amplification method other than PCR.

(d) An analyte labeled for visualization by any of various labeling methods.

Further, a carrier used for preparing a probe carrier such as a DNA chip may be any of those that satisfy the property of carrying out a solid phase-liquid phase reaction of interest. Examples of the carrier include: flat substrates such as a glass substrate, a plastic substrate, and a silicon wafer; a threedimensional structure having an irregular surface; a spherical body such as a bead; and rod-, cord-, and thread-shaped structures. The surface of the carrier may be processed such that a probe can be immobilized thereon. In particular, a carrier prepared by introducing a functional group to its surface to make chemical reaction possible has a preferable form from the viewpoint of reproducibility because the probe is stably bonded in the process of hybridization reaction.

Various methods can be employed for the immobilization of probes. An example of the method of using a combination of a maleimide group and a thiol (—SH) group. In this method, a thiol (—SH) group is bonded to the terminal of a probe, and a process is executed in advance to make the carrier (solid phase) surface have a maleimide group. Accordingly, the thiol group of the probe supplied to the carrier surface reacts with the maleimide group on the carrier surface to form a covalent bond, whereby the probe is immobilized.

First, introduction of the maleimide group can utilize a process of allowing a reaction of a glass substrate with an aminosilane coupling agent and then introducing an maleimide group onto the glass substrate by a reaction of the amino group with an EMCS reagent (N-(6-maleimidocaproyloxy) succinimide, manufactured by Dojindo). Introduction of the thiol group to a DNA can be carried out using 5'-Thiol-Modifier C6 (manufactured by Glen Research Corporation) when the DNA is synthesized by an automatic DNA synthesizer. Instead of the combination of a thiol group and a maleimide group, a combination of, e.g., an epoxy group (on the solid phase) and an amino group (nucleic acid probe terminal), can also be used as a combination of functional groups to be used for immobilization. Surface treatments using various kinds of silane coupling agents are also effective. A probe in which a functional group which can react with a functional group introduced by a silane coupling agent is used. A method of applying a resin having a functional group can also be used.

The detection of pathogenic fungus DNA using the probe carrier of the present invention can be carried out by a DNA-detecting method at least including:

(i) reacting a sample with the probe carrier on which the probe of the present invention is immobilized; and (ii) detecting the reaction intensity of the probe on the probe carrier which is reacted with the nucleic acid contained in the sample.

In addition, the detection can be carried out by a detecting method at least including:

(a) reacting a sample with the probe carrier on which the probe of the present invention is immobilized;

(b) detecting the reaction intensity of the probe on the probe carrier with a nucleic acid in the sample; and (c) specifying the probe reacted with the nucleic acid in the sample when the reaction of the probe with the nucleic acid in the sample is detected and specifying the DNA of a pathogenic fungus in the sample based on the base sequence of the probe.

The probe to be immobilized on the probe carrier is at least one of the above-mentioned items (A) to (P). On the carrier, other probes (those for detecting fungus species other than *Arthroderma benhamiae*) may be immobilized depending on the purpose of test. In this case, the other probes may be those capable of detecting the fungus species other than *Arthroderma benhamiae* without causing cross contamination and the use of such probes allows simultaneous detection of a plurality of fungus species with high accuracy.

As described above, when the base sequence of the ITS region on the DNA sequence of the pathogenic fungus contained in the specimen being amplified by PCR is used as a sample to be reacted with the probe carrier, the primer set for detecting the pathogenic fungus can be used. The primer set is preferably one containing oligonucleotides having the following known base sequences:

(1) 5' tccgtaggtgaacctgcgg 3' (ITS1) (SEQ ID NO. 5); and
(2) 5' tcctccgcttattgatatgc 3' (ITS4) (SEQ ID NO. 6).

Accordingly, the detection method of the present invention may further include amplifying the target nucleic acid in the specimen by PCR using oligonucleotides having the above-mentioned base sequences (1) and (2) as primers.

A kit for detecting a pathogenic fungus can be prepared using at least any of the probes as described above and a reagent for detecting a reaction of the probe with nucleic acid in a sample. The probe in such a kit may be provided as the probe carrier. In addition, the reagent for the detection may contain a primer to be used in labeling for detecting the detection or used in amplification as a pretreatment. In the case where the detection reagent contains the primer, the primer is preferably one suitable for amplifying the DNA of the ITS region of *Arthroderma benhamiae*. Further, the detection reagent may contain a primer for applying the DNA of the ITS region of any pathogenic fungus other than *Arthroderma benhamiae* in addition to the primer for amplifying the DNA of the ITS region of *Arthroderma benhamiae*.

EXAMPLES

Hereinafter, the present invention is described in further details with reference to examples using probes for detecting pathogenic fungi.

Example 1

Production of DNA Chip

In this example, the production of a DNA chip on which the probe of the present invention is immobilized is described.

(1. Preparation of Probe DNA)

First, nucleic acid sequences represented in Table 1 were designed as probes for detecting fungi. Specifically, the probe base sequences represented as follows were selected from the ITS regions on the fungal DNA sequences represented in Table 1. Those probe base sequences are designed so that they will be expected to have extremely high specificities and sufficient hybridization sensitivities without any variation in the respective probe base sequences. Note that the probe base sequences do not have to be limited to the sequences which completely correspond to those represented in Table 1. The base sequences having about 20 to 30 bases each of which include the probe base sequences may be also included in the probe base sequences of Table 1. In this case, other portions other than the base sequences as defined in Table 1 should have base sequences which do not affect the detection accuracy.

TABLE 1

Probe sequence

| Name of fungus | Probe name | SEQ ID NO. | Base sequence |
|---|---|---|---|
| Arthroderma ben- hamiae | P2201 | 1 | 5' agcctctttgggggctttagct 3' |
| | P2202 | 2 | 5' acagacatcaaaaaatcttggaaagctgt 3' |

TABLE 1-continued

Probe sequence

| Name of fungus | Probe name | SEQ ID NO. | Base sequence |
|---|---|---|---|
| | P2203 | 3 | 5' ctgggcgaatgggcagtcaaac 3' |
| | P2204 | 4 | 5' ctctggccttcccccaaatctc 3' |

In each of the probes shown in Table 1, a thiol group was introduced on the 5' terminal of the nucleic acid as a functional group to be immobilized on a DNA chip in accordance with the conventional procedures. After the introduction of the functional group, the probe was purified and then freeze-dried. Subsequently, the freeze-dried probe was stored in a refrigerator at −30° C.

(2. Preparation of PCR Primer)

(2-1. Preparation of PCR Primer for Specimen Amplification)

Conventional primers are used as PCR primers for amplifying the ITS region on DNA to be used for detecting a pathogenic fungus. The conventional primers are shown in Table 2. Specifically, the conventional primers are provided as a set of conventional primers for specifically amplifying the ITS region of DNA, designed from regions common to fungi so as to carry out simultaneous amplification even when fungus species are different.

TABLE 2

Primer sequence

| Primer type | Primer name | SEQ ID NO. | Sequence |
|---|---|---|---|
| Forward Primer | ITS1 | 5 | 5' tccgtaggtgaacctgcgg 3' |
| Reverse Primer | ITS4 | 6 | 5' tcctccgcttattgatatgc 3' |

The primers shown in Table 2 were synthesized and then purified by high-performance liquid chromatography (HPLC). Subsequently, each primer was dissolved in a TE buffer to obtain the primer at a final concentration of 10 pmol/μl.

(2-2. Preparation of PCR Primer for Labeling)

A primer for labeling is prepared by introducing a label into a reverse primer of the primer for specimen amplification. The primer for labeling is shown in Table 3.

TABLE 3

Labeled primer sequence

| Primer type | Primer name | SEQ ID NO. | Sequence |
|---|---|---|---|
| Labeled primer | Cy3-labeled-ITS4 | 7 | 5' tcctccgcttattgatatgc 3' |

The primer shown in Table 3 was labeled with fluorescent dye Cy3. After the synthesis, the primer was purified by high-performance liquid chromatography (HPLC) and then dissolved in a TE buffer to obtain the primer at a final concentration of 10 pmol/μl.

(3. Production of DNA Chip)

(3-1. Cleaning of Glass Substrate)

A glass substrate (size: 25 mm×75 mm×1 mm, manufactured by IIYAMA PRECISION GLASS CO., LTD.) formed of synthetic quartz was placed in a heat- and alkali-resisting rack and immersed in a cleaning solution for ultrasonic cleaning, which was adjusted to have a predetermined concentration. The glass substrate was kept immersed in the cleaning solution for a night and cleaned by ultrasonic cleaning for 20 minutes. The substrate was picked up, lightly rinsed with pure water, and cleaned by ultrasonic cleaning in ultrapure water for 20 minutes. The substrate was immersed in a 1N aqueous sodium hydroxide solution heated to 80° C. for 10 minutes. Pure water cleaning and ultrapure water cleaning were executed again. A quartz glass substrate for a DNA chip was thus prepared.

(3-2. Surface Treatment)

A silane coupling agent KBM-603 (manufactured by Shin-Etsu Chemical Co., Ltd.) was dissolved in pure water at a concentration of 1% by weight (wt %) and stirred at room temperature for 2 hours. Subsequently, the cleaned glass substrate was immersed in the aqueous solution of the silane coupling agent and left standing at room temperature for 20 minutes. The glass substrate was picked up. The surface thereof was lightly rinsed with pure water and dried by spraying nitrogen gas to both surfaces of the substrate. The dried substrate was baked in an oven at 120° C. for 1 hour to complete the coupling agent treatment, whereby an amino group was introduced to the substrate surface. Next, N-maleimidecaproyloxy succinimide (hereinafter abbreviated as EMCS) was dissolved in a 1:1 (volume ratio) solvent mixture of dimethyl sulfoxide and ethanol to obtain a final concentration of 0.3 mg/ml to obtain an EMCS solution. As EMCS, N-(6-maleimidecaproyloxy)succinimide manufactured by Dojindo Laboratories was used.

The baked glass substrate was left standing and cooled and immersed in the prepared EMCS solution at room temperature for 2 hours. By this treatment, the amino group introduced to the surface of the substrate by the silane coupling agent reacted with the succinimide group in the EMCS to thereby introduce the maleimide group to the surface of the glass substrate. The glass substrate picked up from the EMCS solution was cleaned by using the above-mentioned solvent mixture in which the EMCS was dissolved. The glass substrate was further cleaned by ethanol and dried in a nitrogen gas atmosphere.

(3-3. Probe DNA)

The microorganism detection probe prepared in the item (1. Preparation of probe DNA) of Example 1 was dissolved in pure water. The solution was dispensed such that the final concentration (at ink dissolution) was 10 μM. Then, the solution was freeze-dried to remove water.

(3-4. DNA Discharge by BJ Printer and Bonding to Substrate)

An aqueous solution containing 7.5-wt % glycerin, 7.5-wt % thiodiglycol, 7.5-wt % urea, and 1.0-wt % Acetylenol EH (manufactured by Kawaken Fine Chemicals Co., Ltd.) was prepared. Each of the 4 probes (Table 1) prepared in advance was dissolved in the solvent mixture at a predetermined concentration. An ink tank for an inkjet printer (trade name: BJF-850, manufactured by Canon Inc.) is filled with the resultant DNA solution and attached to the printhead. Note that the inkjet printer used here was modified in advance to allow printing on a flat plate. When a printing pattern is input in accordance with a predetermined file creation method, about 5-picoliter of a DNA solution can be spotted at a pitch of about 120 μm. Subsequently, the printing operation was executed for one glass substrate by using the modified inkjet printer to prepare an array. After confirming that printing was reliably executed, the glass substrate was left standing in a humidified chamber for 30 minutes to make the maleimide group on the glass substrate surface react with the thiol group at the nucleic acid probe terminal.

(3-5. Cleaning)

After reaction for 30 minutes, the DNA solution remaining on the surface was cleaned by using a 10-mM phosphate buffer (pH 7.0) containing 100-mM NaCl, thereby obtaining a DNA chip in which single-stranded DNAs were immobilized on the glass substrate surface.

Example 2

Detection of *Arthroderma benhamiae*

In this example, the detection of a microorganism using a two-step PCR method is described.

(1. Extraction of DNA from *Arthroderma benhamiae* (Model Specimen))

(1-1. Culture of Microorganism and DNA Extraction Therefrom)

First, *Arthroderma benhamiae* (standard strain, ATCC 16781) was cultured in accordance with a conventional method. Subsequently, DNA was extracted from the microorganism culture medium and then purified by a nucleic acid purification kit (FastPrep FP100A and Fast DNA Kit, manufactured by Funakoshi Co., Ltd.).

(1-2. Examination of Collected DNA)

The collected DNA of the microorganism (*Arthroderma benhamiae*) was subjected to agarose electrophoresis and absorbance determination at 260/280 nm to examine the qualities of the DNA (i.e., the amount of low-molecular weight nucleic acid as a contaminant and the degree of decomposition) and the collected amount of the DNA. In this example, about 10 μg of DNA was collected, while the degradation of DNA and the contamination of ribosomal RNA were not recognized. The collected DNA was dissolved in a TE buffer to a final concentration of 50 ng/μl and then used in the example described below.

(2. Amplification and Labeling of Specimen)

(2-1. Amplification of Specimen: 1st PCR)

An amplification (1st PCR) reaction of microorganism DNA as an analyte is shown in Table 1 below. The amplification reaction employed the primer set shown in the item (2-1. Culture of microorganism and DNA extraction therefrom) of Example 1, as described above.

TABLE 4

| Composition of 1st PCR reaction solution | |
|---|---|
| TaKaRa ExTaq | 25.0 μL |
| Primer mix | 2.0 μL |
| Forward primer | 1.0 μL |
| Reverse primer | 1.0 μL |
| Template | 1.0 μL |
| Water | up to 50 μL |
| Total | 50 μL |

The amplification reaction was carried out by a commercially-available thermal cycler with the reaction solution of the above-mentioned composition in accordance with the protocol illustrated in FIG. 1.

After completing the reaction, the amplified product was purified using a purification column (QIAquick PCR Purification Kit manufactured by QIAGEN), followed by the quantitative assay of the amplified product.

(2-2. Labeling Reaction: 2nd PCR)

Figure 2:
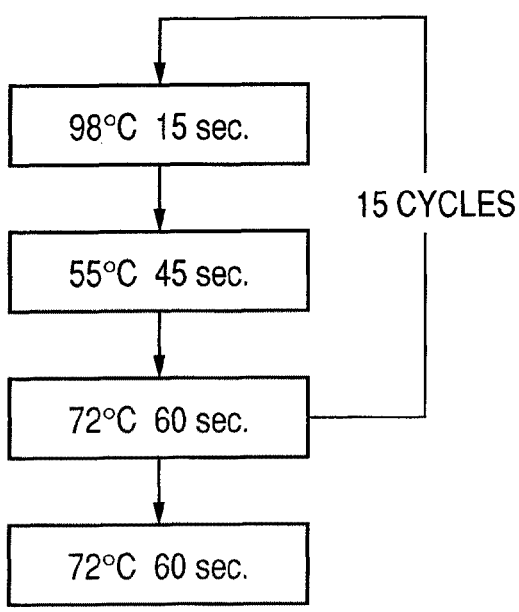
FIG. 2 is a diagram illustrating a 2nd PCR protocol.

A reaction solution of the composition shown in Table 5 was subjected to an amplification reaction with a commercially-available thermal cycler in accordance with the protocol illustrated in FIG. 2. The amplification reaction employed the primer set shown in the item (2-2. Preparation of PCR primer for labeling) of Example 1, as described above.

TABLE 5

| Composition of PCR reaction solution | |
|---|---|
| TaKaRa ExTaq | 25.0 μL |
| Labeled primer | 5.0 μL |
| Template DNA | variable |
| (1st PCR Product) | (30 ng/tube) |
| Water | up to 50 μL |
| Total | 50 μL |

After completing the reaction, the primer was purified using a purification column (QIAquick PCR Purification Kit manufactured by QIAGEN) to obtain a labeled specimen.

(3. Hybridization)

Detection reaction was performed using the DNA chip prepared in the item (3. Preparation of DNA chip) of Example 1 and the labeled specimen prepared in the item (2. Amplification and labeling of specimen) of Example 2.

(3-1. Blocking of DNA Chip)

Bovine serum albumin (BSA, Fraction V: manufactured by Sigma) was dissolved in a 100-mM NaCl/10-mM phosphate buffer such that a 1 wt % solution was obtained. Then, the DNA chip prepared in the item (3. Preparation of DNA chip) of Example 1 was immersed in the solution at room temperature for 2 hours to execute blocking. After completing the blocking, the chip was cleaned using a washing solution as described below, rinsed with pure water and hydro-extracted by a spin dryer.

Washing Solution:
2×SSC solution (300 mM of NaCl, 30 mM of sodium citrate (trisodium citrate dihydrate, $C_6H_5Na_3 \cdot 2H_2O$), pH 7.0) containing 0.1-wt % sodium dodecyl sulfate (SDS).

(3-2. Hybridization)

A drained DNA chip was set on a hybridization device (Hybridization Station, manufactured by Genomic Solutions Inc.) and a hybridization reaction was then carried out using a hybridization solution shown in Table 6 below in accordance with the protocol illustrated in FIG. 3.

TABLE 6

| Composition of hybridization solution | |
|---|---|
| 20 × SSPE | 39.0 μL |
| formamide | 13.0 μL |
| 25 nM positive control | 1.3 μL |
| water | 13.7 μL |
| Template DNA (2nd PCR product) | 50.0 μL |
| 0.5% SDS | 13.0 μL |
| Total | 130.0 μL |

(4. Detection of Microorganism (Fluorescent Assay))

The DNA chip after the above-mentioned hybridization reaction was subjected to a fluorescent assay using a DNA-chip fluorescence detector (GenePix 4000B, manufactured by Axon Co., Ltd.). Consequently, *Arthroderma benhamiae* could be detected with good reproducibility and sufficient signal intensity. The measurement results of *Arthroderma benhamiae* are shown in Table 7 below.

TABLE 7

Measurement results of fluorescence intensity: *Arthroderma benhamiae*

| Probe name | SEQ ID NO. | 1st time Intensity | S/N | 2nd time Intensity | S/N |
|---|---|---|---|---|---|
| P2201 | 1 | 3228.8 | 30.0 | 702.5 | 10.8 |
| P2202 | 2 | 24877.1 | 231.1 | 12014.8 | 185.2 |
| P2203 | 3 | 30529.9 | 283.6 | 12378.8 | 190.9 |
| P2204 | 4 | 27884.7 | 259.0 | 6543.0 | 100.9 |
| BG average | — | 107.7 | — | 64.9 | — |

As shown in Table 7 above, the first to fourth probes for *Arthroderma benhamiae* shown in Table 1 expressed specific hybridization and it was confirmed that there was a nucleic acid sequence in the DNA extract from the microorganism culture medium which has the same sequence as that of the ITS region of the DNA of *Arthroderma benhamiae*. Therefore, it can be concluded that the DNA chip will allow the detection of *Arthroderma benhamiae*.

(5. Results)

As is evident from the above-mentioned description, the above-mentioned examples allowed the preparation of a DNA chip on which a probe set, which was able to detect *Arthroderma benhamiae*, was immobilized. Further, the use of the DNA chip allowed the identification of a pathogenic fungus, so the problems of the DNA probe derived from a microorganism was solved. In other words, the oligonucleotide probe can be chemically produced in large amounts, while the purification or concentration thereof can be controlled. For the purpose of classifying the species of microorganisms, a probe set capable of collectively detecting the same fungus species could be provided. In addition, according to the embodiment, the base sequence of the ITS region on the DNA sequence of the pathogenic fungus can be sufficiently detected and thus the presence of the pathogenic fungus can be effectively determined with high accuracy.

Example 3

Experiment of Other Fungi

This example describes that strong hybridization cannot be detected on any of fungi other than *Arthroderma benhamiae* when the DNA chip prepared in Example 1 is employed.

(1. Extraction of DNA (Model Specimen))

(1-1. Culture of Microorganism and DNA Extraction Therefrom)

The following fungal strains were cultured in a manner similar to Example 2 and the DNA thereof was then extracted and purified. The deposit number of each fungus strain is represented in the parentheses after the name of the fungus.

*Candida albicans* (JCM1542)
*Candida dubliniensis* (ATCC MYA-646)
*Candida glabrata* (JCM 3761)
*Candida guilliermondii* (ATCC 6260)
*Candida intermedia* (ATCC 14439)
*Candida kefyr* (ATCC 42265)
*Candida krusei* (JCM 1609)
*Candida lusitaniae* (ATCC 34449)
*Candida parapsilosis* (JCM 1618)
*Candida tropicalis* (JCM 1541)
*Trichosporon cutaneum* (JCM 1462)
*Trichosporon asahii* (JCM 1809)
*Cryptococcus neoformans* (ATCC 32045)
*Aspergillus fumigatus* (JCM 10253)
*Aspergillus niger* (JCM 10254)
*Epidermophyton floccosum* (ATCC 52063)
*Arthroderma otae* (ATCC 28327)
*Arthroderma gypseum* (ATCC 24163)
*Trichophyton rubrum* (ATCC 10218)
*Trichophyton tonsurans* (ATCC 10217)
*Trichophyton verrucosum* (ATCC 28203)
*Trichophyton violaceum* (ATCC 28944)
*Arthroderma vanbreuseghemii* (ATCC 28145)
*Arthroderma incurvatum* (ATCC 24005)
*Trichophyton interdigitale* (IFM 55365)

(1-2. Examination of Collected DNA)

The collected DNAs of the respective fungi were subjected to the assay of the collected amount thereof as described in Example 2. The collected DNA was dissolved in a TE buffer to have a final concentration of 50 ng/μl and then used in the following example.

(2. Amplification and Labeling of Specimen)

(2-1. Amplification of Specimen: 1st PCR)

An amplification reaction of microorganism DNA to be provided as a specimen was carried out in a manner similar to that of the item (2-1. Amplification of specimen: 1st PCR) of Example 2, as described above. After completing the reaction, the amplified product was purified using a purification column (QIAquick PCR Purification Kit manufactured by QIAGEN), followed by the quantitative assay of the amplified product.

(2-2. Labeling Reaction: 2nd PCR)

A labeling reaction was carried out using the amplified product obtained in the item (2-1. Amplification of specimen: 1st PCR) in a manner similar to that of the item (2-2. Labeling reaction: 2nd PCR) of Example 2, as described above. After completing the reaction, the labeled product was purified using a purification column (QIAquick PCR Purification Kit manufactured by QIAGEN), thereby obtaining a labeled specimen.

(3. Hybridization)

A detection reaction was carried out using the DNA chip manufactured in the item (3. Manufacture of DNA chip) of Example 1, as described above and the labeled specimen prepared in the item (2. Amplification and labeling of specimen) in a manner similar to the item (3. Hybridization) of Example 2, as described above.

(4. Detection of Microorganism (Fluorescent Assay))

A fluorescent assay was carried out in a manner similar to the item (4. Detection of microorganism (fluorescent assay)) of Example 2 as described above. The measurement results of the respective fungal species are shown in Tables 8 to 32 below.

TABLE 8

Measurement results of fluorescence intensity: *Candida albicans*

| Probe name | SEQ ID NO. | 1st time Intensity | S/N | 2nd time Intensity | S/N |
|---|---|---|---|---|---|
| P2201 | 1 | 80.4 | 0.9 | 56.0 | 1.1 |
| P2202 | 2 | 75.9 | 0.9 | 43.5 | 0.9 |
| P2203 | 3 | 81.3 | 0.9 | 45.5 | 0.9 |

TABLE 8-continued

Measurement results of fluorescence intensity: *Candida albicans*

| Probe name | SEQ ID NO. | 1st time Intensity | S/N | 2nd time Intensity | S/N |
|---|---|---|---|---|---|
| P2204 | 4 | 74.7 | 0.9 | 46.9 | 1.0 |
| BG average | — | 86.0 | — | 49.0 | — |

As shown in Table 8 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Candida albicans*.

TABLE 9

Measurement results of fluorescence intensity: *Candida dubliniensis*

| Probe name | SEQ ID NO. | 1st time Intensity | S/N | 2nd time Intensity | S/N |
|---|---|---|---|---|---|
| P2201 | 1 | 84.2 | 0.8 | 54.9 | 1.2 |
| P2202 | 2 | 78.0 | 0.7 | 43.5 | 0.9 |
| P2203 | 3 | 74.1 | 0.7 | 44.9 | 1.0 |
| P2204 | 4 | 66.2 | 0.6 | 44.3 | 0.9 |
| BG average | — | 109.9 | — | 46.7 | — |

As shown in Table 9 above, in the probe set for *Arthroderma benhamiae* shown in Table 1, P0101 and P0102 resulted in comparatively poor hybridization intensities and P0103 and P0104 resulted in substantially no hybridization, compared with the experimental results of Table 7. It can be resulted that a comparison among the intensity patterns of probes P0101, P0102, P0103, and P0104 in Table 7 leads to assess a high possibility of the absence of the genome of *Candida dubliniensis* in a specimen.

TABLE 10

Measurement results of fluorescence intensity: *Candida glabrata*

| Probe name | SEQ ID NO. | 1st time Intensity | S/N | 2nd time Intensity | S/N |
|---|---|---|---|---|---|
| P2201 | 1 | 91.7 | 0.9 | 55.2 | 1.3 |
| P2202 | 2 | 77.9 | 0.8 | 42.1 | 1.0 |
| P2203 | 3 | 99.4 | 1.0 | 43.0 | 1.0 |
| P2204 | 4 | 85.3 | 0.8 | 41.6 | 1.0 |
| BG average | — | 102.8 | — | 43.4 | — |

As shown in Table 10 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Candida glabrata*.

TABLE 11

Measurement results of fluorescence intensity: *Candida guilliermondii*

| Probe name | SEQ ID NO. | 1st time Intensity | S/N | 2nd time Intensity | S/N |
|---|---|---|---|---|---|
| P2201 | 1 | 68.2 | 0.7 | 59.5 | 1.2 |
| P2202 | 2 | 64.0 | 0.7 | 45.5 | 0.9 |
| P2203 | 3 | 67.2 | 0.7 | 46.3 | 1.0 |
| P2204 | 4 | 66.2 | 0.7 | 45.4 | 0.9 |
| BG average | — | 92.8 | — | 48.4 | — |

As shown in Table 11 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Candida guilliermondii*.

TABLE 12

Measurement results of fluorescence intensity: *Candida intermedia*

| Probe name | SEQ ID NO. | 1st time Intensity | S/N | 2nd time Intensity | S/N |
|---|---|---|---|---|---|
| P2201 | 1 | 67.1 | 0.8 | 59.6 | 1.2 |
| P2202 | 2 | 59.4 | 0.7 | 44.7 | 0.9 |
| P2203 | 3 | 56.4 | 0.7 | 46.0 | 1.0 |
| P2204 | 4 | 60.2 | 0.7 | 47.4 | 1.0 |
| BG average | — | 81.4 | — | 48.2 | — |

As shown in Table 12 above, in the probe set for *Arthroderma benhamiae* shown in Table 1, it is evident that any specific hybridization cannot occur in all probes, compared with the experimental results of Table 7 above. It can be concluded that the DNA chip scarcely cross-hybridize to *Candida intermedia*.

TABLE 13

Measurement results of fluorescence intensity: *Candida kefyr*

| Probe name | SEQ ID NO. | 1st time Intensity | S/N | 2nd time Intensity | S/N |
|---|---|---|---|---|---|
| P2201 | 1 | 66.7 | 0.8 | 50.8 | 1.1 |
| P2202 | 2 | 60.8 | 0.8 | 41.7 | 0.9 |
| P2203 | 3 | 60.3 | 0.7 | 42.2 | 0.9 |
| P2204 | 4 | 60.6 | 0.7 | 42.7 | 0.9 |
| BG average | — | 81.0 | — | 45.4 | — |

As shown in Table 13 above, in the probe set for *Arthroderma benhamiae* shown in Table 1, it is evident that any specific hybridization cannot occur in all probes, compared with the experimental results of Table 7 above. It can be concluded that the DNA chip scarcely cross-hybridize to *Candida kefyr*.

TABLE 14

Measurement results of fluorescence intensity: *Candida krusei*

| Probe name | SEQ ID NO. | 1st time Intensity | S/N | 2nd time Intensity | S/N |
|---|---|---|---|---|---|
| P2201 | 1 | 129.4 | 0.8 | 62.2 | 1.3 |
| P2202 | 2 | 116.6 | 0.7 | 44.0 | 0.9 |
| P2203 | 3 | 111.1 | 0.7 | 46.9 | 0.9 |
| P2204 | 4 | 98.8 | 0.6 | 43.6 | 0.9 |
| BG average | — | 168.8 | — | 49.8 | — |

As shown in Table 14 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Candida krusei*.

TABLE 15

Measurement results of fluorescence intensity: *Candida lusitaniae*

| Probe name | SEQ ID NO. | 1st time Intensity | S/N | 2nd time Intensity | S/N |
|---|---|---|---|---|---|
| P2201 | 1 | 79.9 | 0.9 | 62.7 | 1.2 |
| P2202 | 2 | 86.4 | 0.9 | 47.4 | 0.9 |
| P2203 | 3 | 74.8 | 0.8 | 51.2 | 1.0 |
| P2204 | 4 | 81.8 | 0.9 | 50.1 | 1.0 |
| BG average | — | 92.3 | — | 52.1 | — |

As shown in Table 15 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Candida lusitaniae*.

TABLE 16

Measurement results of fluorescence intensity: *Candida parapsilosis*

| Probe name | SEQ ID NO. | 1st time Intensity | S/N | 2nd time Intensity | S/N |
|---|---|---|---|---|---|
| P2201 | 1 | 64.8 | 0.8 | 57.7 | 1.2 |
| P2202 | 2 | 64.4 | 0.8 | 43.0 | 0.9 |
| P2203 | 3 | 60.8 | 0.7 | 45.7 | 0.9 |
| P2204 | 4 | 63.9 | 0.8 | 43.9 | 0.9 |
| BG average | — | 83.1 | — | 48.4 | — |

As shown in Table 16 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Candida parapsilosis*.

TABLE 17

Measurement results of fluorescence intensity: *Candida tropicalis*

| Probe name | SEQ ID NO. | 1st time Intensity | S/N | 2nd time Intensity | S/N |
|---|---|---|---|---|---|
| P2201 | 1 | 61.5 | 0.8 | 55.3 | 1.2 |
| P2202 | 2 | 56.9 | 0.7 | 42.0 | 0.9 |
| P2203 | 3 | 59.5 | 0.7 | 45.6 | 1.0 |
| P2204 | 4 | 60.0 | 0.7 | 43.3 | 0.9 |
| BG average | — | 81.8 | — | 47.6 | — |

As shown in Table 17 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Candida tropicalis*.

TABLE 18

Measurement results of fluorescence intensity: *Trichosporon cutaneum*

| Probe name | SEQ ID NO. | 1st time Intensity | S/N | 2nd time Intensity | S/N |
|---|---|---|---|---|---|
| P2201 | 1 | 72.6 | 0.8 | 63.1 | 1.2 |
| P2202 | 2 | 71.1 | 0.8 | 45.5 | 0.9 |
| P2203 | 3 | 66.5 | 0.8 | 49.7 | 1.0 |
| P2204 | 4 | 71.4 | 0.8 | 49.1 | 1.0 |
| BG average | — | 87.9 | — | 50.8 | — |

As shown in Table 18 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Trichosporon cutaneum*.

TABLE 19

Measurement results of fluorescence intensity: *Trichosporon asahii*

| Probe name | SEQ ID NO. | 1st time Intensity | S/N | 2nd time Intensity | S/N |
|---|---|---|---|---|---|
| P2201 | 1 | 76.7 | 0.9 | 63.2 | 1.2 |
| P2202 | 2 | 69.3 | 0.8 | 48.0 | 0.9 |
| P2203 | 3 | 70.9 | 0.8 | 48.8 | 0.9 |
| P2204 | 4 | 71.1 | 0.8 | 47.9 | 0.9 |
| BG average | — | 90.0 | — | 53.8 | — |

As shown in Table 19 above, in the probe set for *Arthroderma benhamiae* shown in Table 1, it is evident that any specific hybridization does not occur in all probes, compared with the experimental results of Table 7 above. Consequently, It can be concluded that the DNA chip scarcely cross-hybridize to *Trichosporon asahii*.

TABLE 20

Measurement results of fluorescence intensity: *Cryptococcus neoformans*

| Probe name | SEQ ID NO. | 1st time Intensity | S/N | 2nd time Intensity | S/N |
|---|---|---|---|---|---|
| P2201 | 1 | 95.9 | 0.8 | 56.5 | 1.2 |
| P2202 | 2 | 93.8 | 0.8 | 43.1 | 1.0 |
| P2203 | 3 | 91.6 | 0.8 | 48.0 | 1.1 |
| P2204 | 4 | 101.2 | 0.9 | 43.5 | 1.0 |
| BG average | — | 117.2 | — | 45.2 | — |

As shown in Table 20 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Cryptococcus neoformans*.

TABLE 21

Measurement results of fluorescence intensity: *Aspergillus fumigatus*

| Probe name | SEQ ID NO. | 1st time Intensity | S/N | 2nd time Intensity | S/N |
|---|---|---|---|---|---|
| P2201 | 1 | 82.7 | 0.8 | 68.7 | 0.9 |
| P2202 | 2 | 72.6 | 0.7 | 53.4 | 0.7 |
| P2203 | 3 | 74.2 | 0.7 | 54.7 | 0.7 |
| P2204 | 4 | 72.6 | 0.7 | 59.6 | 0.8 |
| BG average | — | 106.8 | — | 73.5 | — |

As shown in Table 21 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Aspergillus fumigatus*.

TABLE 22

Measurement results of fluorescence intensity: *Aspergillus niger*

| Probe name | SEQ ID NO. | 1st time Intensity | S/N | 2nd time Intensity | S/N |
|---|---|---|---|---|---|
| P2201 | 1 | 106.6 | 0.9 | 63.0 | 1.2 |
| P2202 | 2 | 105.3 | 0.9 | 47.0 | 0.9 |
| P2203 | 3 | 86.2 | 0.7 | 49.2 | 1.0 |
| P2204 | 4 | 110.1 | 0.9 | 47.5 | 0.9 |
| BG average | — | 119.1 | — | 50.7 | — |

As shown in Table 22 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Aspergillus niger*.

TABLE 23

Measurement results of fluorescence intensity: *Epidermophyton floccosum*

| Probe name | SEQ ID NO. | 1st time Intensity | S/N | 2nd time Intensity | S/N |
|---|---|---|---|---|---|
| P2201 | 1 | 88.6 | 1.0 | 70.2 | 1.3 |
| P2202 | 2 | 83.4 | 0.9 | 49.5 | 0.9 |
| P2203 | 3 | 121.5 | 1.4 | 57.8 | 1.1 |
| P2204 | 4 | 79.4 | 0.9 | 50.2 | 0.9 |
| BG average | — | 89.7 | — | 53.0 | — |

As shown in Table 23 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Epidermophyton floccosum*.

TABLE 24

Measurement results of fluorescence intensity: *Arthroderma otae*

| Probe name | SEQ ID NO. | 1st time Intensity | S/N | 2nd time Intensity | S/N |
|---|---|---|---|---|---|
| P2201 | 1 | 82.3 | 0.9 | 67.9 | 1.4 |
| P2202 | 2 | 79.7 | 0.8 | 48.3 | 1.0 |
| P2203 | 3 | 78.3 | 0.8 | 53.5 | 1.1 |
| P2204 | 4 | 76.0 | 0.8 | 47.9 | 1.0 |
| BG average | — | 94.2 | — | 49.5 | — |

As shown in Table 24 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Arthroderma otae*.

TABLE 25

Measurement results of fluorescence intensity: *Arthroderma gypseum*

| Probe name | SEQ ID NO. | 1st time Intensity | S/N | 2nd time Intensity | S/N |
|---|---|---|---|---|---|
| P2201 | 1 | 91.6 | 1.0 | 69.8 | 1.3 |
| P2202 | 2 | 148.3 | 1.6 | 55.1 | 1.0 |
| P2203 | 3 | 239.8 | 2.7 | 71.4 | 1.3 |
| P2204 | 4 | 114.0 | 1.3 | 50.7 | 1.0 |
| BG average | — | 90.4 | — | 53.0 | — |

As shown in Table 25 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Arthroderma gypseum*.

TABLE 26

Measurement results of fluorescence intensity: *Trichophyton rubrum*

| Probe name | SEQ ID NO. | 1st time Intensity | S/N | 2nd time Intensity | S/N |
|---|---|---|---|---|---|
| P2201 | 1 | 88.4 | 0.9 | 62.2 | 1.3 |
| P2202 | 2 | 86.8 | 0.9 | 47.9 | 1.0 |
| P2203 | 3 | 162.5 | 1.7 | 58.9 | 1.2 |
| P2204 | 4 | 82.3 | 0.9 | 47.2 | 1.0 |
| BG average | — | 93.2 | — | 49.5 | — |

As shown in Table 26 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Trichophyton rubrum*.

TABLE 27

Measurement results of fluorescence intensity: *Trichophyton tonsurans*

| Probe name | SEQ ID NO. | 1st time Intensity | S/N | 2nd time Intensity | S/N |
|---|---|---|---|---|---|
| P2201 | 1 | 84.0 | 0.8 | 61.9 | 1.3 |
| P2202 | 2 | 93.9 | 0.9 | 44.1 | 0.9 |
| P2203 | 3 | 282.6 | 2.9 | 58.5 | 1.2 |
| P2204 | 4 | 83.3 | 0.8 | 46.4 | 1.0 |
| BG average | — | 99.1 | — | 48.4 | — |

As shown in Table 27 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Trichophyton tonsurans*.

TABLE 28

Measurement results of fluorescence intensity: *Trichophyton verrucosum*

| Probe name | SEQ ID NO. | 1st time Intensity | S/N | 2nd time Intensity | S/N |
|---|---|---|---|---|---|
| P2201 | 1 | 111.9 | 1.0 | 117.6 | 2.1 |
| P2202 | 2 | 898.8 | 8.0 | 920.7 | 16.7 |
| P2203 | 3 | 1110.9 | 9.9 | 1731.7 | 31.4 |
| P2204 | 4 | 1838.7 | 16.4 | 1903.4 | 34.5 |
| BG average | — | 111.9 | — | 55.1 | — |

As shown in Table 28 above, in the probe set for *Arthroderma benhamiae* shown in Table 1, it is evident that strong hybridization does not occur in all probes, compared with the experimental results of Table 7 above. It can be concluded that the DNA chip scarcely cross-hybridize to *Trichophyton verrucosum*.

TABLE 29

Measurement results of fluorescence intensity: *Trichophyton violaceum*

| Probe name | SEQ ID NO. | 1st time Intensity | S/N | 2nd time Intensity | S/N |
|---|---|---|---|---|---|
| P2201 | 1 | 103.4 | 0.9 | 71.4 | 1.4 |
| P2202 | 2 | 95.5 | 0.8 | 49.1 | 0.9 |
| P2203 | 3 | 1174.3 | 10.1 | 678.9 | 12.9 |
| P2204 | 4 | 87.4 | 0.7 | 50.6 | 1.0 |
| BG average | — | 116.6 | — | 52.5 | — |

As shown in Table 29 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Trichophyton violaceum*.

TABLE 30

Measurement results of fluorescence intensity: *Arthroderma vanbreuseghemii*

| Probe name | SEQ ID NO. | 1st time Intensity | S/N | 2nd time Intensity | S/N |
|---|---|---|---|---|---|
| P2201 | 1 | 85.3 | 0.9 | 72.9 | 1.4 |
| P2202 | 2 | 75.7 | 0.8 | 50.2 | 1.0 |
| P2203 | 3 | 132.0 | 1.3 | 99.4 | 1.9 |
| P2204 | 4 | 79.8 | 0.8 | 49.3 | 0.9 |
| BG average | — | 99.4 | — | 52.4 | — |

As shown in Table 30 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Arthroderma vanbreuseghemii*.

TABLE 31

Measurement results of fluorescence intensity: *Arthroderma incurvatum*

| Probe name | SEQ ID NO. | 1st time Intensity | S/N | 2nd time Intensity | S/N |
|---|---|---|---|---|---|
| P2201 | 1 | 107.1 | 1.0 | 59.4 | 1.2 |
| P2202 | 2 | 101.1 | 0.9 | 47.0 | 0.9 |
| P2203 | 3 | 125.7 | 1.1 | 50.0 | 1.0 |
| P2204 | 4 | 91.0 | 0.8 | 46.6 | 0.9 |
| BG average | — | 110.7 | — | 49.6 | — |

As shown in Table 31 above, in the probe set for *Arthroderma benhamiae* shown in Table 1, it is evident that any specific hybridization does not occur in all probes, compared with the experimental results of Table 7 above. It can be concluded that the DNA chip leads low crow hybridization to *Arthroderma incurvatum*.

TABLE 32

Measurement results of fluorescence intensity: *Trichophyton interdigitale*

| Probe name | SEQ ID NO. | 1st time Intensity | S/N | 2nd time Intensity | S/N |
|---|---|---|---|---|---|
| P2201 | 1 | 175.5 | 1.5 | 148.6 | 1.3 |
| P2202 | 2 | 180.3 | 1.6 | 169.4 | 1.5 |
| P2203 | 3 | 348.8 | 3.1 | 318.0 | 2.7 |
| P2204 | 4 | 127.0 | 1.1 | 117.7 | 1.0 |
| BG average | — | 113.5 | — | 49.6 | — |

As shown in Table 32 above, in the probe set for *Arthroderma benhamiae* shown in Table 1, it is evident that any specific hybridization does not occur in all probes, compared with the experimental results of Table 7 above. It can be concluded that the DNA chip scarcely cross-hybridize to *Trichophyton interdigitale*.

As descried above, according to Tables 8 to 32, the DNA chip having a low possibility of accidentally detecting any fungus other than *Arthroderma benhamiae*, on which the probe set for *Arthroderma benhamiae* was immobilized, could be prepared. The use of the DNA chip allows the detection of *Arthroderma benhamiae*. Besides, a probe set which can detect *Arthroderma benhamiae* while distinguishing it from other fungus species could be provided. Further, it has been described that the DNA chip produced in Example 1 can only specifically hybridize with *Arthroderma benhamiae* but not hybridize with any of other fungus species. Therefore, in a DNA chip which is prepared as a combination of the probe for *Arthroderma benhamiae* as described in Example 1 and a probe for other fungus species designed by the same idea as that of the former, a probe set can be provided so that it can not only detect *Arthroderma benhamiae* but also selectively detect *Arthroderma benhamiae* even in a specimen containing a mixture of *Arthroderma benhamiae* with other fungus species.

The present invention is not limited to the above embodiments and various changes and modifications can be made within the spirit and scope of the present invention. Therefore to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-128484, filed May 14, 2007, which is hereby incorporated by reference herein in its entirety.

What is claimed is:

1. A probe set for detecting a DNA of *Arthroderma benhamiae* which is a pathogenic fungus, comprising four probes consisting of the following base sequences (1) to (4) respectively to specifically detect *Arthroderma benhamiae*:
    (1) agcctctttgggggctttagct (SEQ ID NO. 1) or the complementary sequence thereof;
    (2) acagacatcaaaaaatcttggaaagctgt (SEQ ID NO. 2) or the complementary sequence thereof;
    (3) ctgggcgaatgggcagtcaaac (SEQ ID NO. 3) or the complementary sequence thereof; and
    (4) ctctggccttcccccaaatctc (SEQ ID NO. 4) or the complementary sequence thereof.

2. A probe set for detecting a DNA of *Arthroderma benhamiae* which is a pathogenic fungus, comprising the following probes (A) to (D), wherein the probe set does not comprise another probe to detect *Arthroderma benhamiae*:
    (A) a probe consisting of a base sequence represented by agcctctttgggggctttagct (SEQ ID NO. 1) or the complementary sequence thereof;
    (B) a probe consisting of a base sequence represented by acagacatcaaaaaatcttggaaagctgt (SEQ ID NO. 2) or the complementary sequence thereof;
    (C) a probe consisting of a base sequence represented by ctgggcgaatgggcagtcaaac (SEQ ID NO. 3) or the complementary sequence thereof; and
    (D) a probe consisting of a base sequence represented by ctctggccttcccccaaatctc (SEQ ID NO. 4) or the complementary sequence thereof.

3. A probe carrier, comprising the probe set according to claim 1, wherein:
    the probes of the probe set are each immobilized on a carrier; and
    the probes of the probe set are arranged at intervals.

4. A method of detecting a DNA of *Arthroderma benhamiae* in a sample by using a probe carrier, comprising:
    (i) reacting the sample with the probe carrier according to claim 3; and
    (ii) detecting a reaction intensity of a probe on the probe carrier reacted with a nucleic acid contained in the sample.

5. A kit for specifically detecting a DNA of *Arthroderma benhamiae*, comprising:
    the probe set according to claim 1; and
    a reagent for detecting a reaction of a probe with a target nucleic acid.

6. A kit for specifically detecting a DNA of *Arthroderma benhamiae*, comprising:
    the probe set according to claim 2; and
    a reagent for detecting a reaction of a probe with a target nucleic acid.

7. A kit for specifically detecting a DNA of *Arthroderma benhamiae*, comprising:
    the probe carrier according to claim 3; and
    a reagent for detecting a reaction of a probe with a target nucleic acid.

* * * * *